United States Patent
Presura

(10) Patent No.: US 9,910,508 B2
(45) Date of Patent: Mar. 6, 2018

(54) MOVEMENT DETECTION APPARATUS FOR DETECTING A HAND MOVEMENT

(71) Applicant: KONINKLIJKE PHILIPS N.V., Eindhoven (NL)

(72) Inventor: Cristian Nicolae Presura, Veldhoven (NL)

(73) Assignee: Koninklijke Philips, N.V., Eindhoven (NL)

( * ) Notice: Subject to any disclaimer, the term of this patent is extended or adjusted under 35 U.S.C. 154(b) by 0 days.

(21) Appl. No.: 15/115,810

(22) PCT Filed: Feb. 3, 2015

(86) PCT No.: PCT/EP2015/052107
§ 371 (c)(1),
(2) Date: Aug. 1, 2016

(87) PCT Pub. No.: WO2015/121100
PCT Pub. Date: Aug. 20, 2015

(65) Prior Publication Data
US 2017/0031453 A1    Feb. 2, 2017

(30) Foreign Application Priority Data

Feb. 12, 2014 (EP) .................... 14154780

(51) Int. Cl.
*G06F 3/01* (2006.01)
*G06F 3/03* (2006.01)
*G06F 3/0346* (2013.01)

(52) U.S. Cl.
CPC .............. *G06F 3/017* (2013.01); *G06F 3/011* (2013.01); *G06F 3/014* (2013.01); *G06F 3/0304* (2013.01); *G06F 3/0308* (2013.01); *G06F 3/0346* (2013.01)

(58) Field of Classification Search
CPC ........ G06F 3/017; G06F 3/0308; G06F 3/011; G06F 3/0346; G06F 3/014; G06F 3/0304; A61B 5/1126
See application file for complete search history.

(56) References Cited

U.S. PATENT DOCUMENTS

2004/0068409 A1   4/2004   Tanaka et al.
2009/0153477 A1   6/2009   Saenz
(Continued)

FOREIGN PATENT DOCUMENTS

WO   2013126905 A2   8/2013

*Primary Examiner* — Richard Hong

(57) ABSTRACT

The invention relates to movement detection apparatus (1) for detecting a hand movement like a hand gesture which may be used for controlling a computer or another device. A light emitting device emits light into tissue at the wrist (5) of a person and a light detection device detects light, which has travelled through the tissue, at the wrist and generates a light detection signal based on the detected light, wherein a hand movement determination unit determines the hand movement based on the light detection signal. When the hand moves, i.e., for instance, when it rotates or when a finger moves, the composition of the tissue, through which the light travels, and hence the light detection signal change. This change in the light detection signal can be used to reliably determine the respective movement of the hand in a way which is very convenient for the person.

10 Claims, 5 Drawing Sheets

(56) References Cited

U.S. PATENT DOCUMENTS

| | | |
|---|---|---|
| 2009/0174578 A1 | 7/2009 | Taki |
| 2010/0090949 A1 | 4/2010 | Tianqiao et al. |
| 2010/0160834 A1 | 6/2010 | Fong |
| 2011/0054360 A1* | 3/2011 | Son ..................... A61B 5/1126 600/595 |
| 2012/0312956 A1 | 12/2012 | Chang et al. |
| 2014/0028546 A1 | 1/2014 | Jeon et al. |
| 2016/0313791 A1* | 10/2016 | Kirilenko ................ G06F 3/011 |
| 2016/0357265 A1* | 12/2016 | Maani ..................... G06F 3/014 |

* cited by examiner

MOVEMENT DETECTION APPARATUS FOR DETECTING A HAND MOVEMENT

CROSS-REFERENCE TO PRIOR APPLICATIONS

This application is the U.S. National Phase application under 35 U.S.C. § 371 of International Application No. PCT/EP2015/052107, filed on Feb. 3, 2015, which claims the benefit of European Patent Application No. 14154780.2 filed on Feb. 12, 2014. These applications are hereby incorporated by reference herein, for all purposes.

FIELD OF THE INVENTION

The invention relates to a movement detection apparatus, method and computer program for detecting a hand movement. The invention relates further to a system to be controlled by a hand movement.

BACKGROUND OF THE INVENTION

The article "Device Control Using Gestures Sensed from EMG" by Kevin R. Wheeler et al., IEEE International Workshop on Soft Computing in Industrial Applications (2003) discloses a device for measuring electromyographic (EMG) signals of muscles used to perform hand gestures. These signals are then interpreted and translated into computer commands in order to control a computer based on hand gestures.

The muscles for the fingers are arranged at a location in the lower arm close to the elbow such that electrodes of the measuring device need to be connected to the lower arm at this location, in order to measure the EMG signals. However, electrically connecting the measuring device with the muscles in the lower arm of a person just for allowing the person to control a computer is very inconvenient for the person.

SUMMARY OF THE INVENTION

It is therefore an object of the present invention to provide a hand movement detection apparatus, method and computer program which allow for a detection of a hand movement, which is more convenient for a person. It is a further object of the present invention to provide a system to be controlled by a hand movement, which comprises the movement detection apparatus.

In a first aspect of the present invention a movement detection apparatus for detecting a hand movement is presented, wherein the movement detection apparatus comprises:
  a light emitting device for emitting different light beams having different fixed
  a light detection device for detecting light, which has travelled through the tissue, at the wrist and for generating different light detection signals, which correspond to different regions of the tissue, through which the respective light has travelled, based on the detected light, and
  a hand movement determination unit for determining the hand movement based on the different light detection signals.

The hand movement can be a movement of the entire hand like a rotation of the hand. However, the hand movement can also be a movement of a part of the hand relative to another part of the hand like a finger movement. When the hand moves, i.e., for instance, when it rotates or when a finger moves, the tissue composition at the wrist changes which leads to a change in the generated light detection signals. This change in the light detection signals can be used by the hand movement determination unit to reliably determine the respective movement of the hand, wherein, since this determination is based on the light measurement at the wrist of the person, it can be performed in a way which is more convenient for the person.

That the light emitting device emits different light beams having different fixed wavelengths preferentially means that the light emitting device, which may include several light sources, is not a modifiable light emitting device which allows for a modification of the respective wavelength, but, for instance, comprises different light sources emitting different wavelengths, wherein the respective wavelength emitted by the respective light source is fixed.

The light emitting device is preferentially adapted to emit light into the skin tissue through the upper side of the wrist above the tendons of the wrist and the light detection device is preferentially adapted to generate the light detection signal based on light from the skin at the upper side of the wrist above the tendons. The light emitting device can be adapted to emit red light into the tissue. Since red light is not much absorbed by blood and skin tissue, using red light may improve the quality of the light detection signal and thus of the determination of the hand movement. Moreover, the light emitting device may be adapted to emit green light into the tissue. Since it may be assumed that green light has a penetration depth of, for instance, about 3 mm and red light of, for instance, about up to 1 cm, by using green and red light a relatively large depth region within the tissue can be covered, i.e. the hand movement may be reliably determined, irrespective of the depth of the respective tendon relative to the skin.

The light emitting device and the light detection device are adapted to emit light into the tissue at the wrist of the person and to detect light, which has travelled through the tissue, such that at least two different light detection signals are generated, which correspond to different regions of the tissue, through which the respective light has travelled, wherein the hand movement determination unit is adapted to determine the hand movement based on the at least two different light detection signals. In particular, the light emitting device and the light detection device can be adapted such that the different regions of the tissue, through which the respective light has travelled, include different tendons connected to different fingers.

The light emitting device is adapted to emit light into the tissue at different locations on the wrist. Moreover, the light detection device can be adapted to detect light at different locations on the wrist, in order to generate different light detection signals, which correspond to different regions of the tissue, through which the respective light has travelled. These different locations can be above different tendons connecting different fingers with the respective muscles, in order to detect movements of different fingers separately. In particular, the light emitting device and the light detection device may comprise at least two pairs of light sources and light detectors to be arranged at different locations on the wrist, in order to generate at least two different light detection signals, which correspond to different regions of the tissue, through which the respective light has travelled. The hand movement determination unit may be adapted to determine a movement of a first finger based on a first light detection signal, which corresponds to a first region of the tissue, through which the respective light has travelled, and a movement of a second finger based on a second light detection signal, which corresponds to a second region of the tissue, through which the respective light has travelled.

In an embodiment the movement detection apparatus further comprises an attaching element for attaching at least the light emitting device and the light detection device to the wrist of the person. The attaching element is preferentially a wristband. Thus, the movement detection apparatus can be a watch-like device being adapted to detect a hand movement.

The light emitting device is adapted to emit different light beams having different wavelengths into the tissue, which have different penetration depths, in order to generate different light detection signals, which correspond to different regions of the tissue, through which the respective light has travelled. Moreover, the movement detection apparatus may further comprise a movement sensor to be arranged at the wrist of the person, wherein the movement sensor may be adapted to generate a movement signal being indicative of a movement of the entire hand, wherein the hand movement determination unit may be adapted to determine the hand movement based on the light detection signals and based on the movement signal. The movement sensor preferentially includes an accelerometer and/or a gyroscope and/or a magnetometer. Additionally using the movement signal for determining the hand movement can further improve the quality of the hand movement detection.

The hand movement determination unit may be adapted to determine whether the hand movement is a finger movement or a movement of the entire hand based on the light detection signals and the movement signal. For instance, the hand movement determination unit can be adapted to determine whether the hand movement is a finger movement or a movement of the entire hand by comparing the light detection signals with a light detection signal threshold and by comparing the movement signal with a movement signal threshold, wherein the hand movement determination unit can be adapted to determine that the hand movement is a finger movement, if at least one light detection signal, especially all light detection signals, is larger than the light detection signal threshold and if the movement signal is smaller than the movement signal threshold. This allows determining a finger movement more reliably.

The hand movement determination unit may be adapted to provide dependencies between a) light detection signals and optionally also movement signals and b) hand movements and to determine the hand movement based on the provided dependencies and the generated light detection signals and optionally on generated movement signals. The dependencies can be provided as functions, assignments, neural networks et cetera defining a hand movement depending on one or several generated light detection signals and optionally also depending on one or several movement signals.

In an embodiment the hand movement determination unit can be adapted to apply a similarity measure to a) one or several currently generated light detection signals and b) light detection signals stored in the hand movement determination unit, in order to determine the stored one or several light detection signals being most similar to the currently generated one or several light detection signals. The hand movement determination unit can then be adapted to determine the hand movement, which has been assigned to the most similar stored one or several light detection signals. Moreover, the hand movement determination unit can be adapted to apply a similarity measure to a) one or several currently generated light detection signals and to one or several currently generated motion signals and b) light detection signals and motion signals stored in the hand movement determination unit, in order to determine the stored one or several light detection signals and one or several stored motion signals being most similar to the currently generated one or several light detection signals and one or several motion signals. The hand movement determination unit can then be adapted to determine the hand movement, which has been assigned to the most similar stored one or several light detection signals and one or several motion signals.

The hand movement determination unit may be adapted to filter disturbances caused by a physiological property like the heart rate out of the generated light detection signals. For instance, a predefined frequency range, which is known to include the heart rate, may be filtered out of the generated light detection signals, or a frequency or frequency range caused by the physiological property may be determined based on the generated light detection signals by using known standard techniques, which may be based on a Fourier analysis for finding the periodic heart signal, correlation techniques, et cetera, and the determined frequency or frequency range may be filtered out of the generated light detection signals. The hand movement determination unit can then be adapted to determine the hand movement based on the filtered light detection signals.

In a preferred embodiment the movement detection apparatus is operable in a learning mode, in which hand movements to be determined are learned, and in a normal operation mode, in which the movement detection apparatus detects the hand movement. In particular, the light detection device may be adapted to generate one or several light detection signals and optionally also one or several movement signals in the learning mode, while the hand movement is known, wherein the hand movement determination unit may be adapted to, in the learning mode, determine a dependency between a) one or several light detection signals and optionally one or several movement signals and b) a hand movement based on the generated one or several light detection signals, optionally on the one or several movement signals and on the known hand movement. The light detection signal, which is generated while a certain hand movement, i.e. a certain gesture, is performed, may depend on the physiological composition of the wrist of the person and on the exact position of the light emitting device and the light detection device on the wrist. These user-specific conditions can be easily considered, if the dependencies are learned in the learning mode by the respective person.

The movement detection apparatus may further comprise a physiological property determination unit for determining a physiological property of the person based on at least one of the generated light detection signals. The physiological property determination unit may be adapted to determine the heart rate as the physiological property. Thus, the movement detection apparatus may not only be used to detect a hand movement, but it may also be used to detect, for instance, the heart rate. For example, a hand movement, which may also be regarded as being a hand gesture, and optionally also the heart rate or another physiological property may be determined by a watch-like device, which is adapted to be worn at the wrist of the person.

In an embodiment the movement detection apparatus further comprises a sending unit for sending a signal being indicative of the determined hand movement to a device to be controlled depending on the determined hand movement. The device may be a remote device to which the signal may be wirelessly sent.

In another aspect of the present invention a system to be controlled by a hand movement is presented, wherein the system comprises a hand movement detection apparatus for detecting a hand movement as defined in claim 1 and a controller for controlling the system depending on the detected hand movement. Thus, the system, which may be, for instance, a computer system, can be controlled by hand movements, i.e. hand gestures, in a way which is very convenient for a person.

In a further aspect of the present invention a movement detection method for detecting a hand movement is presented, wherein the movement detection method comprises:

emitting different light beams having different fixed wavelengths into tissue at different locations on the wrist of a person by a light emitting device, detecting light, which has travelled through the tissue, at the wrist and generating different light detection signals, which correspond to different regions of the tissue, through which the respective light has travelled, based on the detected light by a light detection device, —determining the hand movement based on the different light detection signals by a hand movement determination unit.

In a further aspect a training method for training the movement detection apparatus is presented, wherein, while carrying out the training method, a certain hand movement is performed and the training method comprises:

emitting light into tissue at the wrist of a person by a light emitting device, detecting light, which has travelled through the tissue, at the wrist and generating a light detection signal based on the detected light by a light detection device, while the certain hand movement is performed, and determining and storing a dependency between the certain hand movement and the generated light detection signal.

In another aspect of the present invention a computer program for detecting a hand movement is presented, wherein the computer program comprises program code means for causing a movement detection apparatus as defined in claim 1 to carry out the steps of the movement detection method as defined in claim 12, when the computer program is run on a computer controlling the movement detection apparatus.

In a further aspect a computer program for training a movement detection apparatus as defined in claim 1 is presented, wherein the computer program comprises program code means for causing the movement detection apparatus to carry out the steps of the training method, when the computer program is run on a computer controlling the movement detection apparatus.

It shall be understood that the movement detection apparatus of claim 1, the system of claim 11, the movement detection method of claim 12, the training method, the computer program of claim 13 and the computer program for training the movement detection apparatus have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The invention relates to movement detection apparatus for detecting a hand movement like a hand gesture which may be used for controlling a computer or another device. A light emitting device emits light into tissue at the wrist of a person and a light detection device detects light, which has travelled through the tissue, at the wrist and generates a light detection signal based on the detected light, wherein a hand movement determination unit determines the hand movement based on the light detection signal. When the hand moves, i.e., for instance, when it rotates or when a finger moves, the composition of the tissue, through which the light travels, and hence the light detection signal change. This change in the light detection signal can be used to reliably determine the respective movement of the hand in a way which is very convenient for the person.

Figure 1:
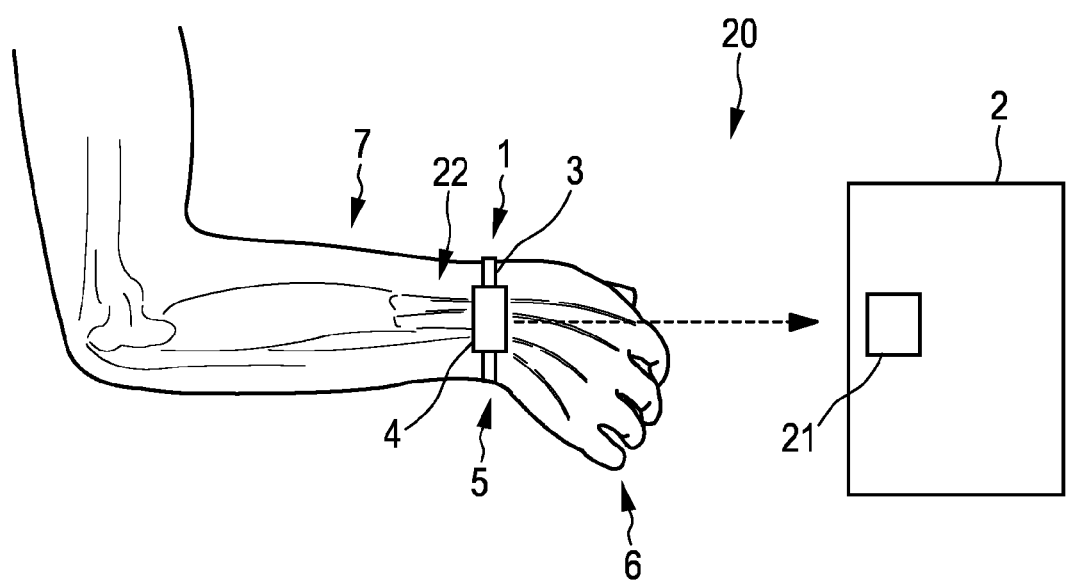
FIG. 1 shows schematically and exemplarily an embodiment of a system comprising a movement detection apparatus for detecting a hand movement and a computer to be controlled by the detected hand movement.

FIG. 1 shows schematically and exemplarily an embodiment of a system to be controlled by hand movements, i.e. by hand gestures. The system 20 comprises a watch-like movement detection apparatus 1 with a wrist band 3 and a casing 4 to be worn at a wrist 5 of a person. Signals, which are indicative of the respective detected hand movement, are sent to a controller 21 of a computer 2, wherein the controller 21 is adapted to control the computer 2 depending on the received signals. The movement detection apparatus 1 can therefore be regarded as being an input device for inputting computer commands into the computer 2, wherein this input device may at least partly replace other input devices like a computer mouse, a keyboard, a touch pad, et cetera.

Figure 2:
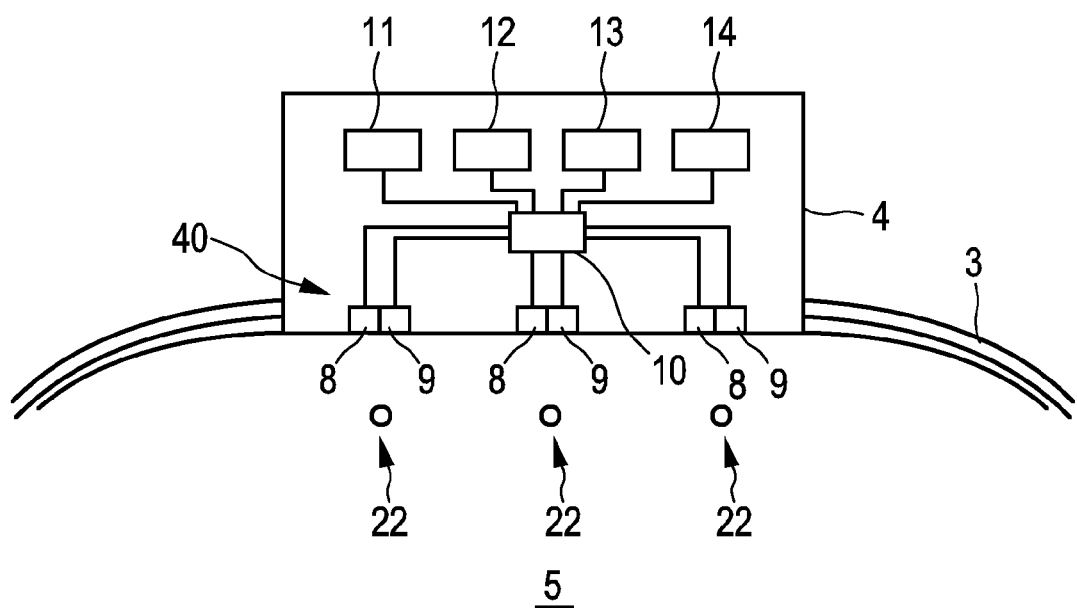
FIG. 2 shows schematically and exemplarily the hand movement detection apparatus in more detail.

The movement detection apparatus 1 comprises a light emitting device for emitting light into tissue at the wrist 5 of the person, a light detection device for detecting light, which has travelled through the tissue, at the wrist 5 and for generating a light detection signal based on the detected light, and a hand movement determination unit for determining the hand movement based on the light detection signal. The light emitting device and the light detection device are adapted to emit light into the tissue at the wrist of the person and to detect light, which has travelled through the tissue, such that several light detection signals are generated, which correspond to different regions of the tissue, through which the respective light has travelled, wherein the hand movement determination unit is adapted to determine the hand movement based on the several light detection signals. In this embodiment the light emitting device and the light detection device are adapted to emit light into the tissue at different locations on the wrist 5 and to detect light at different locations on the wrist 5, in order to generate different light detection signals, which correspond to different regions of the tissue, through which the respective light has travelled. The movement detection apparatus 1 is schematically and exemplarily shown in more detail in FIG. 2.

In this embodiment the light emitting device and the light detection device are formed by several pairs 40 of light sources 8 and light detectors 9 to be arranged at different locations on the wrist 5, in order to generate several light detection signals, which correspond to different regions of the tissue, through which the respective light has travelled. The light sources 8 are light-emitting diodes (LEDs), wherein at least two of the light sources 8 emit light having different wavelengths, i.e. different colors like green and red light. The pairs 40 of light sources 8 and light detectors 9 are arranged above the tendons 22 within the arm 7.

The light sources 8 are adapted to emit light into the skin through the upper side of the wrist 5 above the tendons 22 of the wrist 5, wherein the light detectors 9 are adapted to detect the backscattered and/or reflected light at the skin at the upper side of the wrist 5 above the tendons 22. The movement detection apparatus 1 can therefore be used to pick up tendons' movements, especially in addition to movements of the entire hand which may be detected by using an accelerometer or another additional movement sensor as will be described in the following.

The movement detection apparatus 1 further comprises an accelerometer 13 for generating an acceleration signal, if the wrist 5 and thus the entire hand 6 are moved, wherein the hand movement determination unit 12 is adapted to determine the hand movement based on the generated light detection signals and based on the generated acceleration signal. In particular, the hand movement determination unit 12 can be adapted to compare the light detection signals with a light detection signal threshold and the acceleration signal with an acceleration signal threshold and to determine that the hand movement is a finger movement, if at least one of the generated light detection signals is larger than the light detection signal threshold and if the acceleration signal is smaller than the acceleration signal threshold. If the hand movement determination unit 12 has determined that the hand movement is a finger movement, the finger movement can be more specifically determined based on the generated light detection signals. For instance, the hand movement determination unit 12 can be adapted to provide dependencies between light detection signals and finger movements and to determine a finger movement based on the provided dependencies and the generated light detection signals. The dependencies can be provided as functions, assignments, neural networks et cetera defining a finger movement depending on one or several generated light detection signals. In an embodiment the hand movement determination unit 12 can be adapted to apply a similarity measure to a) currently generated light detection signals and b) light detection signals stored in the hand movement determination unit 12, in order to determine the stored light detection signals being most similar to the currently generated light detection signals. The hand movement determination unit 12 can then be adapted to determine the respective finger movement based on finger movements assigned to the most similar stored light detection signals. The movement determination apparatus 1 further comprises a controller 10 for controlling the different components of the movement detection apparatus 1.

Figure 3:
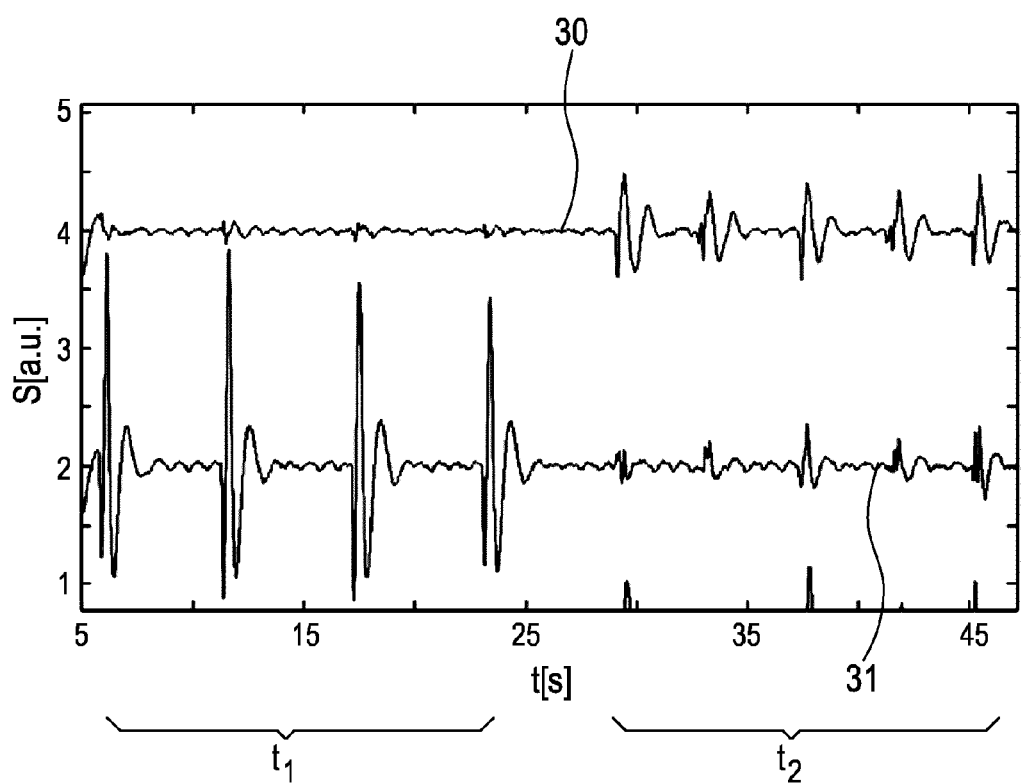
FIG. 3 illustrates two light detection signals generated by the movement detection apparatus.

FIG. 3 shows schematically and exemplarily a first light detection signal 30 and a second light detection signal 31, wherein the amplitude S is illustrated in arbitrary units depending on the time t in s. In the time interval $t_1$ a first finger was moving and in the time interval $t_2$ a second finger was moving. The movement of the first finger is visible in the time interval $t_1$ in the second light detection signal 31 and the movement of the second finger is visible in the time interval $t_2$ in the first light detection signal 30. In the example shown in FIG. 3 the entire hand was not moving, i.e. only the two fingers were moving.

The movement detection apparatus 1 is operable in a learning mode, in which hand movements to be determined are learned in order to train the movement detection apparatus 1, and in a normal operation mode, in which the movement detection apparatus detects the hand movements. For instance, the pairs 40 of light sources 8 and light detectors 9 can be adapted to generate light detection signals in the learning mode, while the hand movement, especially the finger movement, is known, wherein the hand movement determination unit 12 can be adapted to, in the learning mode, determine a dependency between light detection signals and a hand movement based on the generated light detection signals and based on the known hand movement, for instance, by training a neural network. The movement detection apparatus 1 may comprise a switch or another means for allowing the person to select a desired mode of operation. Moreover, it may comprise a display for displaying a hand movement, which should be performed in the learning mode and which may be predetermined and stored in the hand movement determination unit 12, and/or the movement detection apparatus 1 may comprise an input unit allowing a person to input which hand movement will be performed in the learning mode.

The movement detection apparatus 1 can also be adapted use the accelerometer signal and/or a movement signal of another movement sensor, which is indicative of the movement of the entire hand, for training the movement detection apparatus 1. For instance, the pairs 40 of light sources 8 and light detectors 9 can be adapted to generate light detection signals and the accelerometer 13 can be adapted to generate an accelerometer signal in the learning mode, while the hand movement, especially the finger movement, is known, wherein the hand movement determination unit 12 can be adapted to, in the learning mode, determine a dependency between a) light detection signals and an accelerometer signal and b) a hand movement based on a) the generated light detection signals and the generated accelerometer signal and b) based on the known hand movement, for instance, by training a neural network.

The hand movement determination unit 12 can be further adapted to filter disturbances caused by the heart rate out of the generated light detection signals. For instance, a predefined frequency range, which is known to include the heart rate, may be filtered out of the generated light detection signals. The hand movement determination unit 12 can then be adapted to determine the hand movement based on the filtered light detection signals.

The movement detection apparatus 1 further comprises a sending unit 11 for sending a signal being indicative of the determined hand movement to the controller 21 of the computer 2. The controller 21 comprises a corresponding receiving unit such that the controller 21 and the movement detection apparatus 1 can wirelessly communicate with each other. Moreover, the movement detection apparatus 1 may comprise a physiological property determination unit 14 for determining a physiological property of the person based on the generated light detection signals. The determined physiological property may be sent to the computer 2 or to another remote means and/or it may be shown on a display of the movement detection apparatus. Preferentially, the physiological property determination unit 14 is adapted to determine the heart rate as the physiological property. In an embodiment at least one of the light sources 8 emits blue or green light, wherein the physiological property determination unit 14 is adapted to determine the physiological property based on one or several light detection signals generated based on the blue or green light. Moreover, in an embodiment a same wavelength may be used for determining the hand movement and for determining the physiological property, wherein preferentially the influence of the physiological property, especially of the heart rate, is filtered out of the light detection signals, before determining the hand movement. For determining the physiological property based on the generated light detection signals known standard techniques can be used, which may be based on a Fourier analysis for finding the periodic heart signal, correlation techniques, et cetera.

Figure 4:
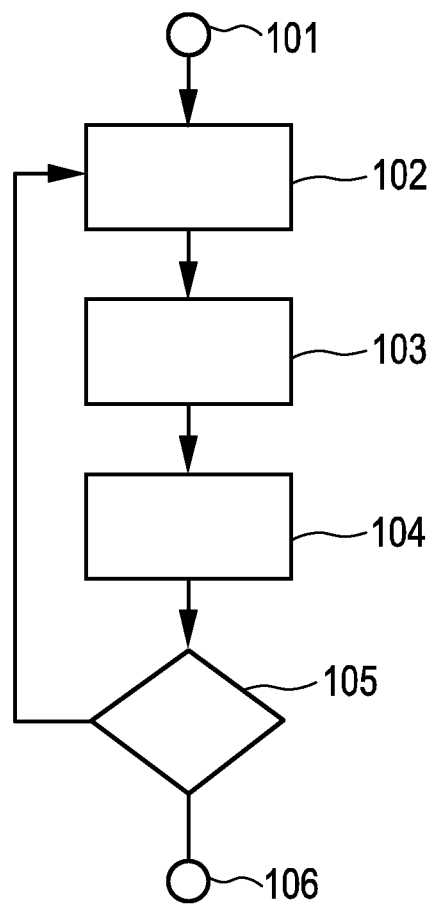
FIG. 4 shows a flowchart exemplarily illustrating an embodiment of a movement detection method for detecting a hand movement.
Figure 5:
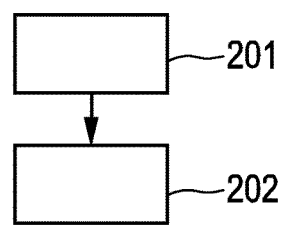
FIG. 5 shows a flowchart exemplarily illustrating an embodiment of a training method for training the movement detection apparatus by learning hand movements.

In the following an embodiment of a movement detection method for detecting a hand movement will exemplarily be described with reference to a flowchart shown in FIG. 4.

In step 101 the movement detection apparatus is initialized and in step 102 the light detection signals and the acceleration signal are measured. In step 103 a hand movement, i.e. a movement of the entire hand or a movement of a part of the hand like a finger with respect to another part of the hand, is determined based on the light detection signals and the acceleration signal, wherein in step 104 a signal being indicative of the determined hand movement is sent to the controller of the computer to be controlled by hand movements, i.e. by hand gestures. In step 105 it is determined whether an abort criterion is fulfilled. The abort criterion may be, for instance, whether a user has switched off the computer 2 and/or the motion detection apparatus 1. If the abort criterion is fulfilled, the motion detection method ends in step 106. Otherwise the method continues with step 102. Steps 102 to 105 are performed in a loop such that continuously light detection signals and the acceleration signal are generated and used to determine a current hand movement, wherein a corresponding signal being indicative of the respective current hand movement is sent to the controller of the computer.

In the following an embodiment of a training method for training the movement detection apparatus by learning hand movements will exemplarily be described with reference to a flowchart shown in FIG. 6.

In step 201 a person performs a certain hand movement and an indication of this hand movement is input into the movement detection apparatus 1, in particular, into the hand movement determination unit 12. Moreover, in step 201, while the hand movement is performed, the light detection signals and the accelerometer signal are generated. In step 202 a dependency between a) the hand movement and b) the generated light detection signals and the generated acceleration signal is determined and stored in the hand movement determination unit 12.

The light emitting device is adapted to emit different light beams having different wavelengths into the tissue, which have different penetration depths, in order to generate different light detection signals, which correspond to different regions of the tissue, through which the respective light has travelled. At least two light sources 8 of the pairs 40 may emit light having different colors as described above. However, in another embodiment, the light sources 8 of the pairs 40 may emit light having the same color and to each pair 40 of light sources and light detectors a further, second light source may be added, which emits light having a wavelength being different to the wavelength of the light emitted by the other, first light source. The movement detection apparatus may be regarded as being a multicolor sensor that is placed on the skin at the wrist location on the upper side just above the tendons.

When the hand moves, i.e. when the entire hand moves, for instance, rotates or when a first part of the hand moves relative to a second part of the hand as it is the case when one or several fingers move, the skin composition under the motion detection apparatus changes, which leads to changes in the detected optical signals, i.e. in the light detection signals. The changes depend on the penetration depth of the light, the configuration of the light sources and light detectors of the movement detection apparatus and the physiological composition of the wrist of the person. The light detection signals are responsive to the movement of the hand, which can be used to determine the hand movement.

In the learning mode the motion detection apparatus is preferentially adapted to learn few basic gestures like a finger pointing gesture or a rotation of the entire hand. After these gestures have been learned, the movement of the hand, for instance, of the entire hand and/or of fingers, will be recognized by the movement detection apparatus and can be interpreted as a gesture input.

Although in above described embodiments the movement detection apparatus comprises a certain configuration of light sources and light detectors, in other embodiments the movement detection apparatus can comprise another configuration of light sources and light detectors. For instance, it can comprise more or less pairs of light sources and light detectors, for instance, it can comprise five pairs, one for each finger. Moreover, distances between light sources and light detectors may be different, in order to generate light detection signals which correspond to different penetration depths.

The accelerometer is preferentially used to distinguish movements of the entire hand like a rotational movement of the hand from other movements like finger movements. If, for example, the accelerometer detects small movements, i.e. if the accelerometer signal is relatively small, but if the light detection signals are relatively large, it may be assumed that the gesture is a finger movement that resulted in a tendon displacement within the skin.

Although in above described embodiments the detected hand movements are used to control a computer, in other embodiments the hand movements can be used to control other devices like a moving machine, a manufacturing apparatus, et cetera. Moreover, in addition to or as an alternative to sending a signal being indicative of the respective detected hand movement to a remote device, the detected hand movement may also be used to control the movement detection apparatus itself. For instance, if the movement detection apparatus is a watch-like apparatus comprising a physiological property determination unit and/or other units like a clock, the detected hand movement may be used to control these units.

Although in the embodiment described above with reference to FIGS. 1 and 2 several certain components are arranged within the casing 4, in other embodiments some of the components may not be arranged within the casing 4, but in a remote device. For instance, the hand movement determination unit 12 may be arranged in a remote device to which the generated light detection signals can be sent by the sending unit.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of a hand movement based on light detection signals and optionally also based on acceleration signals, training the movement detection apparatus, determining a physiological property based on the light detection signals, et cetera performed by one or several units or devices can be performed by any other number of units or devices. These procedures and/or the control of the movement detection apparatus in accordance with the movement detection method and/or in accordance with the learning method can be implemented as program code means of a computer program and/or as dedicated hardware.

A computer program may be stored or distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. A movement detection apparatus for detecting a hand movement, the movement detection apparatus comprising:
    a light emitting device configured to emit light beams having different fixed wavelengths into tissue at different locations above different tendons on the wrist of a person,
    a light detection device configured to detect light, which has travelled through the tissue, at the wrist and to generate different light detection signals, which correspond to different regions of the tissue above different tendons, through which the respective light has travelled, based on the detected light,
    wherein the light emitting device and the light detection device comprise at least two pairs of light sources and light detectors arranged at different locations on the wrist and configured to generate at least two different light detection signals which correspond to different regions of the tissue above different tendons, through which the respective light has travelled, and
    a hand movement determination unit configured to determine the hand movement based on the at least two different light detection signals, wherein the hand movement determination unit is adapted to determine a movement of a first finger based on a first light detection signal generated by a first light detector of the at least two light detectors and which corresponds to a first region of the tissue above a first tendon, through which the respective light has travelled, and a movement of a second finger based on a second light detection signal generated by a second light detector of the at least two light detectors and which corresponds to a second region of the tissue above a second tendon, through which the respective light has travelled.

2. The movement detection apparatus as defined in claim 1, wherein the light emitting device is adapted to emit red and green light into the tissue.

3. The movement detection apparatus as defined in claim 1, wherein the movement detection apparatus further comprises a movement sensor to be arranged at the wrist of the person, wherein the movement sensor is adapted to generate a movement signal being indicative of a movement of the entire hand, wherein the hand movement determination unit is adapted to determine the hand movement based on the light detection signal and based on the movement signal.

4. The movement detection apparatus as defined in claim 1, wherein the hand movement determination unit is adapted to provide dependencies between light detection signals and hand movements and to determine the hand movement based on the provided dependencies and the generated light detection signal.

5. The movement detection apparatus as defined in claim 1, wherein the hand movement determination unit is further adapted to filter disturbances caused by a physiological property out of the generated light detection signals.

6. The movement detection apparatus as defined in claim 1, wherein the movement detection apparatus is operable in a learning mode, in which hand movements to be determined are learned, and in a normal operation mode, in which the movement detection apparatus detects the hand movement.

7. The movement detection apparatus as defined in claim 6, wherein the movement detection apparatus is adapted such that in the learning mode the light emitting device emits light into the tissue at the wrist of the person, the light detection device detects light, which has travelled through the tissue, at the wrist and generates a light detection signal based on the detected light, while a hand movement is performed, and a dependency between the hand movement and the generated light detection signal is determined and stored.

8. The movement detection apparatus as defined in claim 1, wherein the movement detection apparatus further comprises an attaching element for attaching at least the light emitting device and the light detection device to the wrist of the person.

9. A system to be controlled by a hand movement, the system comprising:
    a movement detection apparatus for detecting a hand movement as defined in claim 1, and
    a controller for controlling the system depending on the detected hand movement.

10. A movement detection method for detecting a hand movement, the movement detection method comprising:
    emitting light beams having different fixed wavelengths into tissue at different locations above different tendons on the wrist of a person by a light emitting device,
    detecting light, which has travelled through the tissue, at the wrist and generating different light detection signals, which correspond to different regions of the tissue above different tendons, through which the respective light has travelled, based on the detected light by a light detection device,
    wherein the light emitting device and the light detection device comprise at least two pairs of light sources and light detectors arranged at different locations on the wrist and configured to generate at least two different light detection signals which correspond to different regions of the tissue above different tendons, through which the respective light has travelled,
    determining the hand movement based on the at least two different light detection signals by a hand movement determination unit wherein the hand movement determination unit determines a movement of a first finger based on a first light detection signal generated by a first light detector of the at least two light detectors and which corresponds to a first region of the tissue above a first tendon, through which the respective light has travelled, and a movement of a second finger based on a second light detection signal generated by a second light detector of the at least two light detectors and which corresponds to a second region of the tissue above a second tendon, through which the respective light has travelled.

* * * * *